United States Patent [19]

Huie et al.

[11] 4,441,657

[45] Apr. 10, 1984

[54] DECREASING STATIC CHARGE OF A PARTICULATE SOLID PRODUCT WHICH CAUSES PRODUCT TO PLUG METAL LINE USED FOR PNEUMATIC FLUIDIZED SOLID CONVEYANCE

[75] Inventors: Nicholas C. Huie, Naperville, Ill.; William Bradley, Sullivans Island, S.C.

[73] Assignee: Standard Oil Company (Indiana), Chicago, Ill.

[21] Appl. No.: 311,931

[22] Filed: Oct. 16, 1981

[51] Int. Cl.$^3$ ............................................. B02C 19/12
[52] U.S. Cl. ...................................... 241/14; 241/30
[58] Field of Search .................... 241/14, 24, 30, 22, 241/27, 81; 562/480

[56] References Cited

U.S. PATENT DOCUMENTS

| | | | |
|---|---|---|---|
| 3,186,648 | 6/1965 | Mandle et al. | 241/15 X |
| 3,622,089 | 11/1971 | Quinn | 241/81 X |
| 3,815,833 | 6/1974 | Vliet et al. | 241/15 X |
| 3,998,396 | 12/1976 | Umphrey et al. | 241/81 |
| 4,060,535 | 11/1977 | Cinco | 562/480 |

OTHER PUBLICATIONS

S. L. Soo and S. K. Tong, Powder Technology, 6–1972, pp. 289–294.

*Primary Examiner*—Howard N. Goldberg
*Assistant Examiner*—Timothy V. Eley
*Attorney, Agent, or Firm*—Gunar J. Blumberg; William T. McClain; William H. Magidson

[57] ABSTRACT

Tendency of smooth particles of a size to pneumatically fluidizing from plugging metal transfer conduits is overcome by changing the geometry a portion, at least 10 weight percent of the particles to jagged, rough or sharp particles, as by grinding and blending the changed geometry particles with the remaining smooth particles.

4 Claims, No Drawings

DECREASING STATIC CHARGE OF A PARTICULATE SOLID PRODUCT WHICH CAUSES PRODUCT TO PLUG METAL LINE USED FOR PNEUMATIC FLUIDIZED SOLID CONVEYANCE

This invention relates to overcoming the plugging of metal transfer line by a particulate solid product being conveyed by pneumatically fluidizing of said product which has had a prior history of conveyance by pneumatic fluidization. More particularly this invention pertains to overcoming said plugging when caused by static charge build-up on the particulated solid product by changing of the geometry of some of the particles from smooth to sharp.

BACKGROUND OF THE INVENTION

It is known that static charges accumulating on the surface of materials can be dissipated by providing discharge points or by grounding. It is also known that the accumulation of static charges on or in flowing fluids, even flowing hydrocarbon fractions such as gasoline, can be prevented by grounding of the transfer lines and/or by incorporating "anti-static" compounds or solutes in said fluids. However, such measures for dissipating accumulated or preventing the accumulation of static charges are not feasible for use with particulated solids which must be kept uncontaminated. Also such measures as providing point discharges or grounding are not mechanically feasible for particulate solids, especially crystalline materials which have thousands of particles per unit volume. Such particulate solids can in flow transfer pass over grounding ribbons, wires, etc. with only a minor amount of the particles in contact with such means for grounding dissipation of the static charge. Then there is the problem of providing in some manner the particles with point discharges from particle to particle to some means for charge draw-off so that the point discharges are not destroyed by abrasion as the particles are transferred by fluidized flow.

We have discovered that particulate solids having smooth discrete particles, for example spherical or cylindrical particles, rather than sharp cornered and/or sharp ended particles when transferred as dry product from a drying step to storage, or from storage to shipment or from shipping container to reaction, formulation, packaging, and the like by pneumatic fluidization can accumulate static charges. Such accumulated static charges can cause agglomeration or surface build-up of the particles by physical attraction of dissimilar charges to the extent that the transfer line conveying the particulate solid product becomes restricted to flow and even plugged.

Such flow restriction of transfer line was first noticed when a particulate solid product having smooth discrete particles was being transferred by pneumatic fluidization from a closed hopper car through a metal tube or pipe transfer line having an internal diameter of thousands of times larger than the diameter of the particles. Said product during its manufacture to storage prior to shipment had previously been conveyed from drying to storage and storage to bagging or tote bins and bags for shipment had been transferred as a pneumatically fluidized mass without evidence of static charge build-up or plugging caused thereby.

It was only after use of hopper car shipment that the flow restriction problem occurred during the pneumatic transfer of the product through a rather small, about 10 cm internal diameter, metal transfer line. Such flow restriction caused hopper car unloading time to increase by a factor of 2 to 3 over normal unloading time. Whether the flow restriction was caused by static charge accumulation during manufacture or loading for shipment or only during transfer through the metal line is not known. There were ample contacts of the particles with materials of dissimilar dielectric properties to cause generation of the static charge during manufacture (drying to storage) or shipment (storage to hopper car). But such pneumatic fluidized transfers were through larger diameter metal lines. However, a competitor's product of similar particle size distribution did not suffer the same flow restriction when being unloaded from the closed hopper car by pneumatic fluidization therein and transfer through the metal line of smaller, about 10 cm internal diameter.

Our observation was not of a new phenomenon. Rather, transfer line plugging during pneumatic transport caused by high static charging of the particles was reported in Powder Technology, 6 (1972) pages 283–294 by S. L. Soo and S. K. Tong.

STATEMENT OF THE INVENTION

We have overcome the flow-restricting static build-up on the smooth particles of a mass of particulate solids capable of being fluidized by a gas, that is pneumatically fluidized, for transfer through a conduit (round, elliptical or rectangular) merely by changing the geometry of at least a portion of the smooth particles to jagged, rough or sharp particles.

The portion of the mass of smooth particles which requires changing to jagged, rough or sharp particles to substantially decrease static build-up on the particles can be from all (100 weight percent) down to as low as ten weight percent of the particles. Such particle geometry change can be accomplished by grinding, for example in an impact mill such as a hammer mill. It is advantageous that not all of the particulate mass need be ground to decrease the static charging tendency, which causes pneumatic transfer flow restriction because less energy as well as capital cost is required to grind less than all of the particulate mass.

The tendency for the mass of particles capable of being pneumatically fluidized to accumulate a flow restricting static charge can be measured and expressed in electrical units of coulombs per gram. Such flow restricting charges appear to be in the range of from 3.3 up to $7 \times 10^{-9}$ coulombs per gram. A full flow fluidized particulate mass will have a static charge but only in the range of from 1.0 up to $2.5 \times 10^{-9}$ coulombs per gram. However, by grinding the particulate mass having the high static accumulation causing flow restriction to a product having a static charge accumulation in the 1.0 to $2.5 \times 10^{-9}$ coulumb/gram range and mixing the high tendency with the low tendency static charge accumulating products a non-flow restricting mass can be obtained. Said non-flow restricting blend of the ground and unground products will have even at the 10 weight percent ground and 90 weight percent unground the low static build-up tendency of the full flow mass. This fact is established by the following illustrative examples which also indicate that the particle size of the ground portion of the particulate mass has some bearing on the static accumulation tendency of the mixture or blend of the ground and unground particles. Our invention comprises a method of decreasing the static charge accumulating tendency of a mass of particulate solids having an average particle size sufficient to be pneumatically fluidized, which method comprises grinding or milling a portion of said original mass to sharp, rough particles and blending the ground mass with the remainder of the original mass, including the method wherein the original mass of particulate solids is high purity terephthalic acid having an average particle size of from 185 microns and above, and at least 10 weight percent of said original mass is ground to a particle size of from 40 to 100 microns, and also including the method wherein from 10 to 50 weight percent of the original particulate mass or original high purity terephthalic acid is ground.

EXAMPLES 1 AND 2

The flow restricting masses of particulate solids used herein are of the same high purity (99.9+ weight percent) single chemical compound. Five different particulate products are used to prepare four blends. The five products with their average particle size (AVPS) in microns and their static charge accumulating tendencies are shown in TABLE I. The blend compositions comprising four blends each on a 90%–10% weight basis and the static charge accumulating tendencies of such blends are shown in TABLE II.

TABLE I
UNGROUND AND GROUND HIGH PURITY TEREPHTHALIC ACID

| Product | State | AVPS in Microns | Accumulating Tendency Of Static Charge |
| --- | --- | --- | --- |
| A | Unground | 108 | $4.5 \times 10^{-9}$ coulombs/gm |
| B | Unground | 185 | $3.8 \times 10^{-9}$ coulombs/gm |
| C | Unground | 74 | $0.8 \times 10^{-9}$ coulombs/gm |
| D | Ground | 185 | $0.3 \times 10^{-9}$ coulombs/gm |
| E | Ground | 74 | $0.7 \times 10^{-9}$ coulombs/gm |

TABLE II
BLEND OF 90% PRODUCT A WITH 10% OF PRODUCTS B THROUGH E

| Example | Blends of 90% Product A and | Accumulating Tendency of Static Charge |
| --- | --- | --- |
| Comparative I | 10% Product B | $4.4 \times 10^{-9}$ coulombs/gm |
| Comparative II | 10% Product C | $3.7 \times 10^{-9}$ coulombs/gm |
| Illustrative 1 | 10% Product D | $3.9 \times 10^{-9}$ coulombs/gm |
| Illustrative 2 | 10% Product E | $1.3 \times 10^{-9}$ coulombs/gm |

EXAMPLE 3

In the following examples blends were made consisting of 80 weight percent of Product F and 20 weight percent of Product G as Comparative III and of 80 weight percent Product F and 20 weight percent Product H as Example 3 Blend. Product F is unground and has average particle size greater than 185 microns while Product G is ground and has average particle size of 185 microns and Product H is also ground and has an average particle size of 47 microns. The static charge accumulating tendencies of the blends are shown in TABLE III.

TABLE III
BLENDS OF 80% UNGROUND AND 20% GROUND HIGH PURITY TEREPHTHALIC ACID

| Material | Accumulating Tendency of Static Charge |
| --- | --- |
| Product F | $6.1 \times 10^{-9}$ coulombs/gm |
| Product G | $4.9 \times 10^{-9}$ coulombs/gm |
| Product H | $2.4 \times 10^{-9}$ coulombs/gm |
| Comparative III | $5.5 \times 10^{-9}$ coulombs/gm |
| Example 3 Blend | $2.4 \times 10^{-9}$ coulombs/gm |

The blends of Examples 1, 2, and 3 have the requisite low static charge accumulating tendencies to be full flowing, that is not to cause restrictive slowing to plugging of flow.

The practice of the concept of this invention can be effected by diverting a portion, suitably 10 to 50 weight percent and preferably 10 to 30 weight percent of the high static charge accumulating particulate mass to grinding and milling when the mass of particulate solids is being transported either to storage or to shipping. The diverted portion of the transported particulate solids is then ground or milled to sharp, rough particles having a static accumulating tendency downward from $2.5 \times 10^{-9}$ coulombs/gram, for example sharp, rough particles of average particle size of from 40 to 70 microns. Such ground or milled portion can be pneumatically fluidized and so transported to be joined with the unground 50 to 90 weight percent portioned for blending before reaching product storage or shipment.

The invention claimed is:

1. A method of decreasing the static charge accumulating tendency of a mass of high purity terephthalic acid having an average particle size of from 185 microns and above which method comprises grinding at least 10 weight percent of the high purity terephthalic acid to sharp, rough particles having a particle size of from about 40 to about 100 microns and blending the ground mass of terephthalic acid with the mass of unground purified terephthalic acid.

2. The method of claim 1 wherein from 10 to 50 weight percent of the unground particulate mass is ground.

3. A method of decreasing the static charge accumulating tendency of a mass of purified terephthalic acid having an average particle size of from 185 microns and above, which method comprises milling at least 10 weight percent of the unmilled terephthalic acid to sharp, rough particles having a particle size of about 40 to about 100 microns and blending the milled mass of purified terephthalic acid with the remainder of the unmilled purified terephthalic acid.

4. The method of claim 3 wherein from 10 to 50 weight percent of the unground particulate mass is ground.

* * * * *